United States Patent [19]

Kawamura et al.

[11] 4,283,475

[45] Aug. 11, 1981

[54] PENTAMETHINE THIOPYRYLIUM SALTS, PROCESS FOR PRODUCTION THEREOF, AND PHOTOCONDUCTIVE COMPOSITIONS CONTAINING SAID SALTS

[75] Inventors: Koichi Kawamura; Harumi Katsuyama; Hideo Sato, all of Asaka, Japan

[73] Assignee: Fuji Photo Film Co., Ltd., Minami-ashigara, Japan

[21] Appl. No.: 180,058

[22] Filed: Aug. 20, 1980

[30] Foreign Application Priority Data

Aug. 21, 1979 [JP] Japan .................................. 54-105548
Nov. 5, 1979 [JP] Japan .................................. 54-142034

[51] Int. Cl.³ .............................................. G03G 5/09
[52] U.S. Cl. ......................................... 430/70; 430/81; 430/83; 430/95; 430/37; 542/400; 430/73; 430/76; 430/82
[58] Field of Search ....................... 430/81, 82, 83, 95, 430/70, 73, 76; 542/400

[56] References Cited

U.S. PATENT DOCUMENTS

| | | | |
|---|---|---|---|
| 3,184,516 | 5/1965 | Chechak et al. | 542/400 X |
| 3,250,615 | 5/1966 | Van Allan et al. | 430/95 X |
| 3,617,268 | 11/1971 | Murakami et al. | 542/400 X |
| 3,896,112 | 7/1975 | Kubota et al. | 430/81 X |
| 3,938,994 | 2/1976 | Reynolds et al. | 430/81 X |

FOREIGN PATENT DOCUMENTS

| | | | |
|---|---|---|---|
| 49-16503 | 4/1974 | Japan | 430/82 |
| 49-53050 | 5/1974 | Japan | 430/83 |
| 52-2296 | 1/1977 | Japan | 430/83 |

Primary Examiner—Roland E. Martin, Jr.
Attorney, Agent, or Firm—Sughrue, Mion, Zinn, Macpeak and Seas

[57] ABSTRACT

2,6-Di-tert-butyl-4-[5-(2,6-di-tert-butyl-4H-thiopyran-4-ylidene)penta-1,3-dienyl]thiopyrylium salts, which are novel, colorless, transparent, having an adsorption in the far infrared to near infrared region and capable of imparting high sensitivity to photoconductive substance; process for producing the salts; and a photoconductive composition containing the salt.

29 Claims, 3 Drawing Figures

FIG. 1

WAVE LENGTH (nm)

FIG. 2

WAVE LENGTH (nm)

FIG. 3

WAVE LENGTH (nm)

PENTAMETHINE THIOPYRYLIUM SALTS, PROCESS FOR PRODUCTION THEREOF, AND PHOTOCONDUCTIVE COMPOSITIONS CONTAINING SAID SALTS

BACKGROUND OF THE INVENTION

1. Field of the Invention

This invention relates to novel pentamethine thiopyrylium salts, i.e. 2,6-di-t-butyl-4-[5-(2,6-di-t-butyl-4H-thiopyran-4-ylidene)penta-1,3-dienyl]thiopyrylium salts, a process for production thereof, and to photoconductive compositions containing them.

2. Description of the Prior Art

Thiopyrylium and pyrylium dyes are known to be useful in various applications. For example, they are used as an electron acceptor compound in direct positive photographic silver halide emulsions disclosed in Japanese Patent Publication No. 40900/71; or as spectral sensitizers for photoconductive materials, particularly spectral sensitizers for organic photoconductive materials, as described in Davis et al. U.S. Pat. No. 3,141,700, van Allan et al. U.S. Pat. No. 3,250,615, Reynolds et al. U.S. Pat. No. 3,938,994, and Research Disclosure No. 16321, page 5, November 1977.

Photoconductors sensitized with thiopyrylium and pyrylium dyes are used in the various applications disclosed in the above-cited patent documents, and are especially important for xerography or electrofax-type electrophotography.

The use of these known thiopyrylium dyes as sensitizers for photoconductive materials, however, cannot provide colorless, transparent photoconductive compositions because these dyes have an absorption band in the visible region.

SUMMARY OF THE INVENTION

It is an object of this invention to provide novel thiopyrylium compounds which are colorless, transparent and have an absorption in the far infrared to near infrared region and impart high sensitivity to photoconductive substances, and a process for producing said compounds.

Another object of this invention is to provide a photoconductive composition comprising a photoconductive substance and, as a sensitizer, a novel thiopyrylium compound which imparts high sensitivity to the photoconductive substance.

The thiopyrylium salts of this invention are 2,6-di-t-butyl-4[5-(2,6-di-t-butyl-4H-thiopyran-4-ylidene)penta-1,3-dienyl]thiopyrylium salts of the following chemical formula:

wherein $Z^{\ominus}$ represents an anion, and X represents a hydrogen atom, a halogen atom, an alkyl group or an aryl group.

DETAILED DESCRIPTION OF THE INVENTION

In formula (I) representing the novel thiopyrylium salt of this invention, the anions represented by $Z^{\ominus}$ are known single atomic ions or atomic grouping ions composed of a plurality of atoms which have a negative charge. Anions of strong acids represented by HZ and having a pKa of not more than 5, especially not more than 2, are preferred for easy synthesis of the thiopyrylium salts. Specific examples of the anions are single atomic ions such as halogen anions, e.g. fluoride, chloride, bromide and iodide ions; and ionic groups, for example organic anions such as trifluoroacetate, trichloroacetate and p-toluenesulfonate ions, and inorganic anions such as perchlorate, periodate, tetrachloroaluminate, trichloroferrate (II), tetrafluoroborate, hexafluorophosphate, sulfate, hydrogensulfate and nitrate ions. Divalent anions are interpreted, as a matter of formality, such that ½ of such an anion represents a monovalent anion. Among the above-exemplified anions, chloride, bromide, perchlorate, tetrafluoroborate, p-toluenesulfonate and trifluoroacetate ions are preferred.

The halogen represented by X includes fluorine, chlorine, bromine and iodine, chlorine and bromine being preferred. The alkyl group represented by X includes, for example, linear or branched alkyl groups having 1 to 15 carbon atoms, preferably 1 to 5 carbon atoms, such as methyl, ethyl, isopropyl, t-butyl and pentyl groups, which may be substituted. Examples of the substituent for the alkyl group are aryl groups having 6 to 15 carbon atoms, preferably 9 to 13 carbon atoms such as phenyl, tolyl, ethylphenyl and naphthyl groups; halogen atoms, that is chlorine, bromine, fluorine and iodine; and alkoxy groups having 1 to 5 carbon atoms, preferably 1 to 3 carbon atoms, such as a methoxy group. Specific examples of aryl-substituted alkyl groups are benzyl, (4-methylphenyl)methyl, (2-methylphenyl)methyl, phenethyl and (1-naphthyl)methyl groups.

The aryl group represented by X includes a phenyl group and aryl groups having 6 to 11 carbon atoms, preferably 6 to 8 carbon atoms, optionally bearing a substituent. The substituent for the aryl group includes, for example, halogen atoms such as chlorine and bromine, alkoxy groups having 1 to 5 carbon atoms, preferably 1 to 3 carbon atoms, such as a methoxy group; and alkyl groups having 1 to 5 carbon atoms, preferably 1 to 3 carbon atoms. Specific examples of the aryl group include phenyl, o-, m- and p-tolyl, 2,3-, 2,4- and 2,5-xylyl and ethylphenyl groups.

Preferred thiopyrylium salts of this invention are given below. It should be understood that the invention is in no way limited to these specific examples.

The thiopyrylium salts of this invention have their main absorption in the far infrared to near infrared regions (in the neighborhood of 650 to 900 nm), and do not substantially absorb visible light. When these salts are used as sensitizing dyes for organic photoconductive substances, which do not absorb visible light (e.g., poly-N-vinylcarbazole), colorless, transparent photoconductive materials can be produced. Accordingly, when a layer of an organic photoconductive substance containing the thiopyrylium salt of this invention is formed on the surface of white paper, the paper exhibits the appearance of plain paper having no coated layer. The photosensitive material comprising an organic photoconductive substance containing the thiopyrylium salt of this invention is useful in ordinary electrophotography using a tungsten-filament lamp as a light source. Since it has sensitivity in the far infrared to near infrared region, it is especially effective in electrophotography using a light source within this region (e.g., a semiconductor laser). The thiopyrylium salt of this invention can also be effectively utilized as photoconductive photosensitive particles by incorporating it in photoconductive photosensitive particles in photoelectrophoretic photography. Another superior characteristic of the compound of this invention is that a photosensitive material comprising the compound of this invention has high sensitivity.

The thiopyrylium salt of this invention may be produced by the following processes.

[Process 1]

This process comprises reacting a 2,6-di-t-butyl-4-methylthiopyrylium salt [compound (II)] with a 1-phenylamino-3-phenylimino-1-propene [compound (III)] or a salt of the compound (III) with an acid.

In the above formulae, $Z^{\ominus}$ and X are the same as defined above. Preferred examples of the compound of formula (III) are 1-phenylamino-3-phenylimino-1-propene, 2-benzyl-1-phenylamino-3-phenylimino-1-propene, 2-phenyl-1-phenylamino-3-phenylimino-1-propene, 2-bromo- or 2-chloro-1-phenylamino-3-phenylimino-1-propene, and 2-ethyl-1-phenylamino-3-phenylimino-1-propene.

The acid forming a salt with the compound (III) is an acid having a pKa generally not more than 4, preferably not more than 1, and includes, for example, hydrochloric acid, hydrobromic acid and sulfuric acid.

The above reaction is carried out either in a carboxylic acid anhydride or in an amine. When the reaction is carried out in the carboxylic acid anhydride, the carboxylic acid anhydride contributes to the reaction system as an aniline-eliminating agent. As a carboxylic acid anhydride an aliphatic carboxylic acid anhydride containing 4 to 16 carbon atoms and which may be substituted with one or more substituents, may be used. The substituents include halogen atoms, such as fluorine and chlorine. Specific examples of the carboxylic acid anhydride include acetic acid anhydride, propionic acid anhydride and trifluoro acetic acid anhydride. In order to dissolve the reaction materials, there may be added an auxiliary solvent which does not react with the raw materials, the carboxylic acid anhydride, the base described hereinafter and the reaction product in the reaction system, such as acetic acid or nitrobenzene. This reaction requires the presence of a base. The base is generally an organic base, for example alkali metal acetates such as sodium acetate or potassium acetate; alkylamines, preferably primary amines having 1 to 10 carbon atoms, secondary amines having 2 to 20 carbon atoms total or tertiary amines having 3 to 30 carbon atoms; aromatic amines; and nitrogen-containing aromatic amines. Specific examples are triethylamine, piperidine, aniline, dimethylaniline, pyridine, and quinoline.

The amount of the base used is 0.2 to 100 moles, preferably 0.5 to 20 moles, per mole of the 2,6-di-t-butyl-4-methylthiopyrylium salt. The weight ratio of the carboxylic acid anhydride to the 2,6-di-t-butyl-4-methylthiopyrylium salt is 0.1–100:1, preferably 1–50:1.

When the reaction is carried out in an amine, an auxiliary solvent such as acetic acid or nitro-benzene may likewise be added. The amine used in this reaction may be the same as those exemplified above as the base. The amount of amine is generally about 0.5 to 200 moles, preferably 1 to 100 moles per mole of the 2,6-di-t-butyl-4-methylthiopyrylium salt.

Process 1 is generally carried out at about 50° to 200° C., preferably 80° to 140° C. The amounts of compounds (II) and (III) may be stoichiometric. Generally, about 0.3 to 1 mole of the 1-phenylamino-3-phenylimino-1-propene is used per mole of the 2,6-di-t-butyl-4-methylthiopyrylium salt. The reaction time varies depending upon the reaction temperature, the type of the solvent, etc., but is generally 1 minute to 1 hour.

[Process 2]

This process comprises reacting a 2,6-di-t-butyl-4-methylthiopyrylium salt with a 1,1,3,3-tetraalkoxypropane of the structural formula (IV).

(RO)$_2$CH—CHX—CH(OR)$_2$ ⟶ Compound (I)

(IV)

wherein R represents an alkyl group having 1 to 4 carbon atoms, and X represents the same group as defined with respect to the compound (III).

Examples of suitable compound (IV) include 1,1,3,3-tetramethoxypropane, 1,1,3,3-tetraethoxypropane, 2-methyl- or 2-ethyl-1,1,3,3-tetramethoxypropane, and 2-bromo- or 2-chloro-1,1,3,3-tetraethoxypropane.

The reaction is carried out in a carboxylic acid or a carboxylic acid anhydride in the presence of an amine. As a carboxylic acid and a carboxylic acid anhydride an aliphatic carboxylic acid anhydride described in [Process 1] and an aliphatic acid corresponding thereto may be used. Specific examples of the acid and acid anhydride include acetic acid, propionic acid, trifluoroacetic acid and anhydride thereof. The amount of the carboxylic acid or carboxylic acid anhydride is about 0.1 to 100 parts by weight, preferably about 1 to 50 parts by weight, per part by weight of the 2,6-di-t-butyl-4-methylthiopyrylium salt.

The amine used may be the same as those exemplified in Process 1. The amount of the amine is generally 0.5 to 200 moles, preferably 1 to 100 moles, per mole of the 2,6-di-t-butyl-4-methylthiopyrylium salt. The reaction temperature is generally about 50° to 200° C., preferably about 80° to 140° C.

The amounts of the thiopyrylium salt and the tetraalkoxypropane may be stoichiometric, but generally, 0.5 to 10 moles of the latter is used per mole of the former. The reaction time varies depending upon the reaction conditions such as the reaction temperature, but is generally about 1 minute to 1 hour.

Compound (II) used in Processes 1 and 2 may be produced, for example, from 2,6-di-t-butyl-4H-pyran-4-one [compound (i)] through the following reactions.

Compound (i) is heated in the presence of phosphorus pentasulfide at Step (1) according to the process described in *The Chemistry of the Carbonyl Group* Chapter 17, E. Campaigne Inperscience Publisher 1966, (page 1075) to obtain compound (ii). The reaction product, Compound (ii) is then reacted with alkali hydrosulfide such as potassium hydrosulfide in a solvent at a temperature between 50° C. to 200° C. in an atmosphere of an inert and oxygen-free gas such as $N_2$, $CO_2$, and argon gas (Step 2) to produce compound (iii). The solvent used at Step 2 is water-free and non aqueous solvent having at least 20 of dielectric constant and at least 2 of dipole moment, for example, hexamethyl phosphoric triamide, dimethylsulfoxide, N,N-dimethylformamide or N-methylpyrrolidone. The alkali sulfide or alkali hydrosulfide used is 1 to 30 moles, preferably 3 to 20 moles, per 1 mole of compound (ii). Compound (iii) is then reacted with an alkylating agent at Step 3 to obtain compound (iv) which is then hydrolyzed to form compound (v) [Step 4]. The reaction temperature at Step (3) is $-10°$ C. to 200° C., preferably 40° C. to 100° C. and the reaction time is 30 minutes to 2 hours. In formula (iv), $R_4$ is an alkyl or substituted alkyl group derived from the alkylating agent.

Examples of such alkylating agents are methyl halide such as methyl iodide, methyl bromide, methyl chloride and methyl fluoride, trimethyloxonium tetraborate, dimethylsulfuric acid and methylfluorosulfate, ethyl halide such as ethyl iodide and ethyl bromide, ethyl-p-toluene sulfonate, diethylsulfuric acid and triethyloxonium tetrafluoroborate, benzyl halide such as benzyl chloride, benzyl bromide and benzyl iodide, benzyl-p-toluene sulfonate, and usually known alkylating agents. The amount of an alkylating agent is 1 to 50 moles per 1 mol of compound (iii), preferably 1 to 20 moles. Solvent, for example, ketone such as acetone, methylethylketone, acetonitrile, and halogenized hydrocarbon such as chloroform may be used and the alkylating agent is also used as a solvent.

The hydrolysis is carried out for 10 minutes to 10 hours in water or in a mixture of water and a solvent which is miscible with water and having high polarity at least 20 of dielectric constant and at least 1 of dipole moment, such as an alcohol, e.g., methanol, ethanol, an ether, e.g., 1,4-dioxane, an amino, e.g., hexamethyl phosphoric triamide, acetonitride, dimethylsulfoxide, sulfolane, etc. A mixture containing 0.001 equivalent or more of water per 1 equivalent of a solvent is used in the latter case. The hydrolysis temperature is preferably 80° C. to 100° C. A catalyst for hydrolysis may be used such as acidic catalyst having not more than 5 of pKa value, for example, hydrochloric acid, trifluoroacetic acid, etc., and basic catalyst having at least 9 of pKa value, for example, ammonia, sodium hydroxide, etc.

Alternatively, compound (v) may be obtained directly by hydrolysis of compound (iii) in the same manner as described above. In this hydrolysis other than acidic and basic catalysts $HgCl_2$, $Ag_2CO_3$, $Pb(CH_3CO_2)_2$ and HgO may be used.

Compound (v) is subjected to the action of a Grignard reagent at a temperature of $-20°$ C. to 25° C. for 30 to 90 minutes in a solvent and in a nonoxidizing atmosphere and then treated with an acid to form compound (II) (Step 5).

Preferred Grignard reagents are methylmagnesium iodide, methylmagnesium bromide and methylmagnesium chloride. In place of these Grignard reagents, other organometallic compounds such as methylpotassium, methylsodium, methyllithium, methylcalciumiodide, dimethylberyllium, trimethylaluminum and trimethylboron can be used. The organometallic compound is used in an amount between 1 mole and about 10 moles, preferably 1 to 3 moles per mole of compound of formula (iii).

Non-aqueous solvents containing substantially no water can be used as the solvent in the reaction of Step (5). Examples of such non-aqueous solvents are ether compounds such as dimethyl ether, methyl ethyl ether, diethyl ether, dimethoxyethane, tetrahydrofuran and 1,4-dioxane, aromatic compounds such as benzene and toluene, and saturated hydrocarbon compounds such as pentane, hexane, cyclohexane, methylcyclohexane and petroleum ether.

Preferred acids for use in the above reaction are acids capable of forming the anion group $Z^\ominus$, such as hydrofluoric acid, hydroiodic acid, hydrochloric acid, hydrobromic acid, perchloric acid, tetrafluoroboric acid, hexafluorophosphoric acid, sulfuric acid, nitric acid, trichloroacetic acid, trifluoroacetic acid and p-toluensulfonic acid.

By the term "non-oxidizing atmosphere" is meant rare gases typified by helium and argon and inert gases typified by nitrogen. These gases replace air to form a substantially oxygen-free condition under which the reaction is carried out. The pressure of the rare gas or inert gas may be in the neighborhood of atmospheric pressure, but this is just one example of the reaction pressure and suitable values may be selected depending on the case.

Compound (i) can be synthesized by the method of described in Reynolds, Journal of Heterocyclic Chemistry, vol. 11, page 1075, 1974.

A detailed description of the individual steps of the above process is given in the following patent applications of the present inventors. For steps (1) and (2), see Japanese Patent Application No. 81523/79; for step (3), see Japanese Patent Application No. 81525/79; for step (3'), see Japanese Patent Application No. 81524/79; for step (4), see Japanese Patent Application No. 81525/79; and for step (5), see Japanese Patent Application No. 37249/79.

The thiopyrylium salts of this invention are used as sensitizers for inorganic and organic photoconductive substances in order to improve their photoconductivity and sensitivity characteristics. Zinc oxide is cited as an example of the inorganic photoconductive substance. Organic photoconductive substances are especially effective, however.

In some cases that thiopyrylium salt of the present invention does not sensitize an inorganic photoconductive materials, such as zinc oxide, as satisfactorily as the salt sensitizes an organic photoconductive material. As a reason for this, it is believed that the salt from an inorganic photoconductive material occurs in presence of a materials other than the salt and the inorganic photoconductive material, such as a binder, because the affinity of the thiopyrylium salt for the inorganic photoconductive material is smaller as compared with the affinity of the salt for an organic photoconductive material. In such a case, by dispersing an inorganic photoconductive material (for example zinc oxide) into a resinous binder which does not have polar groups (such as carboxyl groups or hydroxyl groups) having strong affinity for the inorganic photoconductive material, a sufficient sensitizing effect can be obtained. It is preferable to use a resinous binder which has substantially no polar groups in its molecules, such as a polystyrene, a styrene-butadiene copolymer in an electrophotographic material containing an inorganic photoconductive material such as zinc oxide.

Examples of the organic photoconductive substances are low-molecular compounds, for example carbazoles such as carbazole and N-ethylcarbazole; triarylamines such as tri-p-tolylamine and triphenylamine; polyarylmethanes of the following formula wherein n is an integer of 2 to 4, m is an integer of 0 to 2, and $R_1$, $R_2$ and $R_3$ represent a hydrogen atom, an alkyl group such as methyl, ethyl or propyl, or an aryl group such as phenyl or tolyl; fused aromatic cyclic compounds such as anthracene; aromatic compounds having an unsaturated bond such as tetraphenylbutadiene or tetraphenylhexatriene; and unsaturated heterocyclic ring-containing compounds such as oxaziazole, thiaziazole, triazole, imidazole, pyrazoline and the derivatives thereof; and high-molecular compounds, such as, poly-N-vinylcarbazole, poly-N-vinylcarbazole derivatives such as brominated poly-N-vinylcarbazole, polyvinylanthracene, polyacenaphthylene, polyvinylacridine, and polyvinyl phenothiazine (cf. Research Disclosure, Vol. 109, pages 62–63, Sec. 4, May, 1973). Preferred among these photoconductive substances are triarylamines such as tri-p-tolylamine and triphenylamine; poly-N-vinylcarbazole; polyarylmethanes such as 4,4'-bis(diethylamino)-2,2'-dimethyltriphenylmethane; and unsaturated heterocyclic ring-containing compounds typified by pyrazoline derivatives such as 3-(4-dimethylaminophenyl)-1,5-diphenyl-2-pyrazoline.

The photoconductive composition of this invention comprising the thiopyrylium salt of this invention as a sensitizer is obtained by dissolving or dispersing such a thiopyrylium dye and such a photoconductive substance in an organic solvent. The composition is used as a photosensitive material by coating it on an electrically conductive support by usual methods such as rotary coating, blade coating, knife coating, reverse roll coating, dip coating, rod bar coating or spray coating and then drying the coating. Alternatively, particles are produced from the aforesaid organic solvent solution using, for example, a mini-spray device, and dispersed in an insulating liquid to form a dispersion which is used in photoelectrophoresis.

The electrically conductive support may include paper; an aluminum-paper laminate; metal foils such as an aluminum or zinc foil; metal plates such as plates of aluminum, copper, zinc, brass and a zinc-plated metal; and materials obtained by vacuum-depositing a metal such as chromium, silver, nickel or aluminum on an ordinary photographic film base such as cellulose acetate or polystyrene. Preferably used are materials obtained by vacuum-depositing a metal such as chromium, silver, nickel, aluminum or indium oxide on a sheet of paper, a cellulose acetate film or a polyethylene terephthalate film.

The organic solvent used to form the photoconductive composition of this invention is a volatile hydrocarbon solvent having a boiling point of not more than 200° C. In particular, halogenated hydrocarbons having 1 to 3 carbon atoms, such as dichloromethane, chloroform, 1,2-dichloroethane, tetrachloroethane, dichloropropane and trichloroethane, are preferred. There can also be used various other solvents used in coating compositions, for example aromatic hydrocarbons such as chlorobenzene, toluene, xylene or benzene; ketones such as acetone or 2-butanone; ethers such as tetrahydrofuran, and methylene chloride, and mixtures of these solvents. The solvent is added in an amount of about 1 to 100 g, preferably about 5 to 20 g, per gram of the dye, photoconductive substance and other additives combined.

The amount of the sensitizer in accordance with this invention is about 0.0001 to 30 parts by weight, preferably about 0.001 to 10 parts by weight, per 100 parts by weight of the photoconductive substance.

In one mode of using the composition of this invention, the sensitizer is included in particles used for photoelectrophoresis, and an image can be obtained by photoelectrophoresis. The particles used in photoelectrophoresis can be prepared from a solution comprising a photoconductive substance such as poly-N-vinyl carabazole, the sensitizer of this invention, etc. by using a mini-spraying device. Usually, the solution contains the photoconductive substance in an amount of 0.1 to 10% by weight. The weight ratio of the sensitizer to the photosensitive substance is the same as described above. These particles usually having a diameter of 1 μm to 10 μm are further dispersed in an insulating liquid containing a saturated hydrocarbon such as decane, dodecane, octane, paraffin or iso-octane, preferably a long-chain alkyl hydrocarbon such as Isopar E, Isopar H or Isopar G (trademarks for products of Esso Chemical Company), and the resulting dispersion is used in photoelectrophoresis. Isopar E, Isopar H and Isoper G contain 99.9% by weight, 99.3% by weight and 99.8% by weight, respectively, of saturated hydrocarbons and 0.05% by weight, 0.2% by weight and 0.2% by weight, respectively, of aromatic hydrocarbons. Isopar H further contains not more than 0.5% by weight of olefins. These hydrocarbons have a boiling point of 115°–142° C., 174°–189° C. and 158°–177° C., respectively. The amount of the particles in a suitable dispersion is about 0.5 to 10% by weight, preferably about 1 to 3% by weight, based on the weight of the dispersion.

The photoelectrophoretic method and devices used therefor are described in Japanese Patent Publication No. 20640/70 which corresponds to U.S. Pat. No. 3,473,940.

Additives optionally may be incorporated as required to improve the properties of the photoconductive layer and the particles. For example, the photoconductive composition of this invention may further contain an electrically insulating binder. Film-forming hydrophobic polymeric binders having a fairly high insulating strength are preferred for use in the photoconductive composition of this invention. Typical examples of such binders include vinyl resins; natural resins such as gelatin, cellulose ester derivatives and cellulose nitrate; polycondensates including polyesters and polycarbonates; silicone resins; alkyd resins including styrene-alkyd resin; paraffins; and various mineral waxes. Examples of specified polymers useful as binders are described in Research Disclosure, Vol. 109, pages 61-67, under the title "Electrophotographic Elements, Materials and Methods".

The amount of the binder incorporated in the photoconductive composition of this invention generally varies. Typically, the useful amount of the binder is about 10 to about 90% by weight based on the total weight of the mixture of the photoconductive material and the binder.

In producing photoconductive particles, a charge regulating agent and a dispersion stabilizer can also be added. Especially advantageously used are a copolymer of lauryl methacrylate and styrene (in a weight ratio of 4–2:1) and a copolymer of 2-ethylhexyl methacrylate and styrene (in a weight ratio of 4:2–1) which have the dual function of charge regulation and dispersion stabilization.

In order to improve flexibility and strength, a plasticizer such as chlorinated diphenyl, dimethyl phthalate and epoxy resins (available under the tradenmme "Epikote" series) may be added in an amount of up to 60 parts by weight, preferably 10 to 40 parts by weight, per 100 parts by weight of the photoconductive substance.

The thickness of a coated layer of the photoconductive composition of this invention on a suitable support can vary. Usually, the composition can be coated in a thickness ranging from about 10 microns to about 300 microns (before drying). It is possible to form a substantially colorless transparent layer of the photoconductive composition having an optical density to visible light of not more than about 0.05. The preferred coating thickness prior to drying has been found to be in the range of about 50 microns to about 150 microns. Beneficial results, however, can also be obtained outside this range. The thickness of the coating after drying may be from about 2 microns to about 50 microns. However, even when the coated layer of the photoconductive composition has a thickness after drying from about 1 micron to about 200 microns, it is colorless and transparent to visible light and is sensitive only to the far infrared to near infrared region.

The synthesis of the starting compound (II) is illustrated below.

SYNTHESIS EXAMPLE (1) Preparation of 2,6-di-tert-butyl-4H-pyran-4-thione

[Compound (ii)]

34.6 g of 2,6-di-tert-butyl-4H-pyran-4-one was dissolved in 240 ml of anhydrous benzene, and 73 g of phosphorus pentasulfide was added thereto. The mixture was heated at the reflux temperature for 2.5 hours with stirring.

After the reaction, the benzene solution was removed by decantation. Aqueous ammonia was added to the residue to decompose the phosphorus pentasulfide, followed by extraction with diethyl ether and drying over anhydrous sodium sulfate. The solvent was distilled off under reduced pressure from the benzene solution, and the residue was extracted with hexane and concentrated to obtain 16.0 g of compound (ii) as reddish crystals. The ethereal extract and the oily material left after extraction with hexane were combined and passed through a silica gel column (eluent: benzene) for purification to further give 6.8 g of compound (ii) as crystals.

(2) Preparation of 2,6-di-tert-butyl-4H-thiopyran-4-thione

[Compound (iii)]

6.64 g of compound (ii) was dissolved in 330 ml of hexamethylphosphoric triamide, and an argon gas was passed through the solution for 20 minutes.

The mixture was stirred over an oil bath at 85° to 90° C., and 19.8 g of sodium hydrosulfide (prepared by vacuum drying about 70% $NaSH.xH_2O$, a product of Wako Pure Chemical Industries, Ltd., over phosphorus pentoxide at 70° to 80° C. for one day) was added in an argon atmosphere over a period of 30 minutes.

The stirring was continued at the same temperature for 1.5 hours, and the reaction solution was thrown into water to terminate the reaction. The resultant crystals were filtered, dried and recrystallized from hexane to afford 1.78 g (yield 25%) of compound (iii).

(3) Preparation of 2,6-di-tert-butyl-4-(methylthio)thiopyrylium iodide

[Compound (iv)]

1.55 g of the compound (iii) was refluxed together with 20 ml of acetone and 5 ml of methyl iodide for 1 hour.

After the solvent was distilled off under reduced pressure, the residue was recrystallized from acetone to give 1.55 g (yield 63%) of compound (iv) as prism-like red crystals.

(4) Preparation of 2,6-di-tert-butyl-4H-thiopyran-4-one

[Compound (v)]

1.30 g of 2,6-di-tert-butyl-4-(methylthio)thiopyrylium iodide [compound (iv)] was stirred on an oil bath at 85° to 90° C. together with 10 ml of dimethyl sulfoxide and 1 ml of water for 13 hours.

The reaction solution was thrown into water, and the mixture was extracted with diethyl ether. The diethyl ether solution was dried over anhydrous sodium sulfate, and the solvent was distilled off under reduced pressure. The residue was passed through an alumina column using benzene-diethyl ether (1:1 by volume) mixed solvent to give 740 mg (yield 97%) of compound (v) as crystals. The resultant crystals were recrystallized from cyclohexane.

(5) Preparation of 2,6-di-tert-butyl-4-methylthiopyrylium perchlorate

[Compound (II)]

550 mg of 2,6-di-tert-butyl-4H-thiopyran-4-one [compound (v)] was dissolved in 20 ml of diethyl ether in an argon atmosphere, and then 8.6 ml of a solution of methyl magnesium iodide in diethyl ether (2.7 millimoles) was added dropwise to the solution under cooling at about −10° C. After the addition, the mixture was stirred for a period of 45 minutes at room temperature (about 23° C.), and a saturated aqueous solution of ammonium chloride was added. The ether solution was decanted, and the diethyl ether was distilled off under vacuum. Then, 20 ml of 35% perchloric acid was added to the residue, and the mixture was warmed on a water bath to form crystals. The crystals were filtered, washed with cold water and then with diethyl ether, and dried. There were obtained 470 mg (yield 63%) of crystals. Recrystallization from ethanol gave 2,6-di-tert-butyl-4-methylthiopyrylium perchlorate [compound (II)] as colorless crystals having a melting point of 192° to 193° C.

The following Examples illustrate the present invention more specifically.

EXAMPLE 1

Synthesis of 2,6-di-tert-butyl-4-[5-(2,6-di-tert-butyl-4H-thiopyran-4-ylidene)-penta-1,3-dienyl]thiopyrylium perchlorate [compound (1)] by process 1

0.193 g of 2,6-di-tert-butyl-4-methylthiopyrylium perchlorate (compound II) and 0.160 g of 1-phenylamino-3-phenylimide-1-propene were heated at 100° C. for 3 minutes in a test tube. To the mixture were added 0.193 g of the compound (II), 0.24 g of sodium acetate and 1 ml of acetic anhydride, and they were heated at 100° C. for 30 minutes. After the reaction mixture was allowed to cool, 50 ml of diethyl ether was added to precipitate crystals. The crystals were filtered, and dried. Recrystallization from ethanol gave 0.22 g of needle-like crystals having a melting point of 232° C.

The product was determined to be compound (1) by the following elemental analysis and spectral data.

Elemental analysis for $C_{31}H_{45}S_2ClO_4$:

|  | C | H | S |
| --- | --- | --- | --- |
| Calculated: | 64.06% | 7.80% | 11.03% |
| Found: | 63.95% | 7.85% | 10.93% |

Infrared absorption spectrum (wave number $cm^{-1}$) 1480, 1460, 1130, 730.

Proton NMR spectrum (chemical shift, unit ppm, tetramethyl silane as a reference, in deuterochloroform, +24° C.): 1.44 (S, 36H), 7.48 (S, 4H), 8.35 (d, d, 2H, J=12.5, J=13.7), 6.51 (t, 1H, J=12.5), 6.28 (d, 2H, J=13.7) [S, d and t respectively represent a singlet, a doublet and a triplet; d, d represents two sets of doublet; the figure before H represents the area ratio; and J represents a coupling constant in Hz.]

Electronic spectrum wavelength (nm) (in acetonitrile; the figures in parentheses show extinction coefficients): 805 (235,000), 746 (91,000), 440 (4,600), 354 (13,000), 304 (8,000), 252 (5,300).

Figure 1:
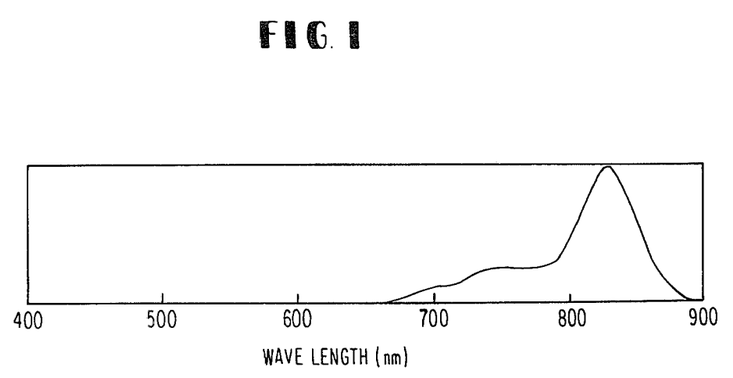
FIG. 1 is an absorption spectrum of the thiopyrylium salt of the invention obtained in Example 1 in a film of poly-N-vinylcarbazole.
Figure 2:
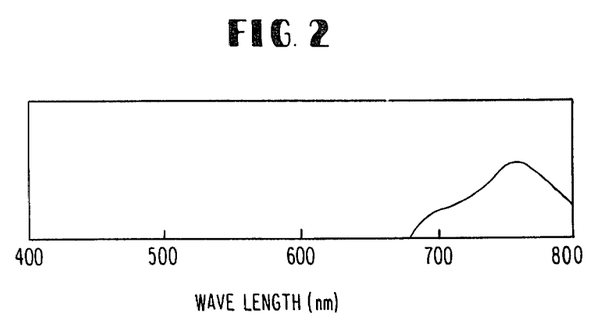
FIG. 2 is a spectral sensitivity spectrum of a poly-N-vinylcarbazole film containing the thiopyrylium salt obtained in Example 1 as a sensitizer.

The absorption spectrum of the compound (1) in a film of poly-N-vinylcarbazole is shown in FIG. 1, and the spectral sensitivity spectrum of a film of poly-N-vinylcarbazole containing the compound (1) as a spectral sensitizer is shown in FIG. 2. The amount of the compound (1) was 1.5 mg per gram of the poly-N-vinylcarbazole.

Figure 3:
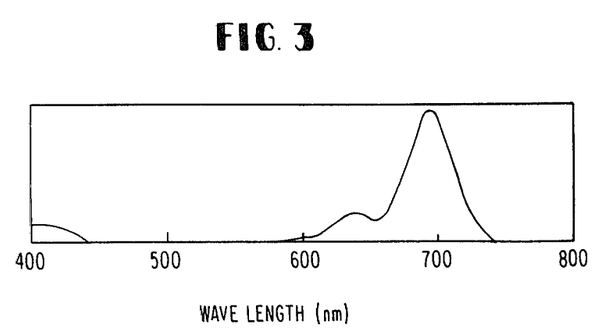
FIG. 3 is an absorption spectrum of a known pyrylium compound in dichloromethane.

For comparison, FIG. 3 shows the absorption spectrum of a pyrylium compound of the following chemical formula which is described in the Research Disclosure cited hereinabove in dichloromethane.

It is seen from these charts that the compound of this invention has substantially no absorption in the visible region and is substantially colorless and transparent, and a photoconductive composition containing it as a sensitizer has sensitivity in the far infrared to near infrared region. On the other hand, a photoconductive composition containing the compound described in the Research Disclosure has sensitivity in the far red region, but as shown in FIG. 3, has an absorption in the visible region. Thus, a photoconductive material containing this compound as a sensitizer is colored.

EXAMPLE 2

Synthesis of 2,6-di-tert-butyl-4-[5-(2,6-di-tert-butyl-4H-thiopyran-4-ylidene)penta-1,3-dienyl]thiopyrylium perchlorate [compound (1)] by process 2

0.03 g of 2,6-di-tert-butyl-4-methylthiopyrylium perchlorate [compound (II)] and 0.1 g of 1,1,3,3-tetraethoxypropane [compound (IV)] were dissolved in 0.3 ml of acetic acid in a test tube. Pyridine (0.2 ml) was added, and the mixture was heated over an oil bath at 125° C. for 10 minutes.

After the reaction mixture was allowed to cool, 20 ml of diethyl ether was added to precipitate crystals. The crystals were filtered, and recrystallized from ethanol to afford 0.015 g of crystals having a melting point of 232° C.

The infrared absorption spectrum and electronic spectrum of the product were the same as those of the product obtained in Example 1.

EXAMPLE 3

Synthesis of 2,6-di-tert-butyl-4-[3-benzyl-5-(2,6-di-tert-butyl-4H-thiopyran-4-ylidene)penta-1,3-dienyl]thiopyrylium perchlorate [compound (5)] by process1

60 mg of 2,6-di-tert-butyl-4-methylthiopyrylium perchlorate and 60 mg of 2-benzyl-1-phenylimino-3-phenylimide-1-propene were heated in 1 ml of acetic anhydride over an oil bath at 110° C. for 5 minutes.

After the heating, 60 mg of 2,6-di-tert-butyl-4-methylthiopyrylium perchlorate and 100 mg of sodium acetate were added, and the mixture was heated over an oil bath at 110° C. for 10 minutes.

After the reaction mixture was allowed to cool, 50 ml of diethyl ether was added. The precipitated crystals were filtered, and recrystallized from ethanol to afford 25 mg (yield 20%) of crystals having a melting point of 221° to 222° C.

Elemental analysis for $C_{38}H_{51}S_2ClO_4$:

|  | C | H | S |
|---|---|---|---|
| Calculated: | 67.98% | 7.66% | 9.55% |
| Found: | 68.05% | 7.68% | 9.30% |

Infrared absorption spectrum (wave number cm$^{-1}$): 1482, 1180, 1135, 738.

Electronic spectrum (nm) [in acetonitrile]: 803 (5.34), 742 (4.89), 442 (3.82), 364 (4.35), 310 (3.98).

EXAMPLE 4

Synthesis of 2,6-di-tert-butyl-4-[3-phenyl-5-(2,6-di-tert-butyl-4H-thiopyran-4-ylidene)penta-1,3-dienyl]thiopyrylium perchlorate [compound (4)] by process 1

64 mg of 2,6-di-tert-butyl-4-methylthiopyrylium perchlorate and 60 mg of 2-phenyl-1-phenylimino-3-phenylimide-1-propene were heated in 1 ml of acetic anhydride over an oil bath at 110° C. for 5 minutes.

After heating, 65 mg of 2,6-di-tert-butyl-4-methylthiopyrylium perchlorate and 100 mg of sodium acetate were added, and the mixture was heated over an oil bath at 110° C. for 10 minutes.

After the reaction mixture was allowed to cool, 50 ml of diethyl ether was added. The precipitated crystals were filtered, and recrystallized from ethanol to afford 30 mg (yield 23%) of crystals having a melting point of 214° to 215° C.

Elemental analysis for $C_{37}H_{49}S_2ClO_4$:

|  | C | H | S |
|---|---|---|---|
| Calculated: | 67.60% | 7.51% | 9.75% |
| Found: | 67.49% | 7.63% | 9.50% |

Infrared absorption spectrum (wave number cm$^{-1}$): 1480, 1160, 740.

Electronic spectrum (nm) [in acetonitrile]: 806 (5.32), 744 (4.88), 444 (3.79), 364 (4.39), 310 (3.97).

EXAMPLE 5

Synthesis of 2,6-di-tert-butyl-4-[3-methyl-5-(2,6-di-tert-butyl-4H-thiopyran-4-ylidene)penta-1,3-dienyl]thiopyrylium perchlorate [compound (2)] by process 2

121 mg of 2,6-di-tert-butyl-4-methylthiopyrylium perchlorate and 350 mg of 2-methyl-1,1,3,3-tetraethoxypropane were heated in a mixture of 1 ml of acetic acid and 1 ml of pyridine over an oil bath at 125° C. for 10 minutes.

After the reaction mixture was allowed to cool, 50 ml of diethyl ether was added. The precipitated crystals were filtered, and dried to afford 100 mg (yield 45%) of crystals.

Recrystallization from ethanol afforded 53 mg of crystals having a melting point of 225° to 226° C.

Elemental analysis for $C_{32}H_{47}S_2ClO_4$:

|  | C | H | S |
|---|---|---|---|
| Calculated: | 64.56% | 7.96% | 10.77% |
| Found: | 64.30% | 7.88% | 10.45% |

Infrared absorption spectrum (wave number cm$^{-1}$): 1485, 1158, 740.

Electronic spectrum (nm) [in acetonitrile]: 809 (5.33), 744 (4.90), 446 (3.77), 360 (4.30), 311 (4.01).

EXAMPLE 6

Synthesis of 2,6-di-tert-butyl-4-[3-bromo-5-(2,6-di-tert-butyl-4H-thiopyran-4-ylidene)penta-1,3-dienyl]thiopyrylium perchlorate [compound (7)] by process 1

50 mg of 2,6-di-tert-butyl-4-methylthiopyrylium perchlorate and 60 mg of 2-bromo-1-phenylimino-3-phenylimide-1-propene were heated in 1 ml of acetic anhydride over an oil bath at 110° C. for 5 minutes.

After the heating, 50 mg of 2,6-di-tert-butyl-4-methylthiopyrylium perchlorate and 150 mg of sodium acetate were added, and the mixture was heated over an oil bath at 110° C. for 15 minutes.

After the reaction mixture was allowed to cool, 50 ml of diethyl ether was added. The precipitated crystals were filtered, and recrystallized from ethanol to afford 5 mg (yield 3%) of crystals having a melting point of 224° to 225° C.

Elemental analysis for $C_{31}H_{44}S_2ClBrO_4$:

|  | C | H | S |
|---|---|---|---|
| Calculated: | 56.40% | 6.72% | 9.71% |
| Found: | 56.51% | 6.68% | 9.55% |

Infrared absorption spectrum (wave number cm$^{-1}$): 1485, 1140, 740.

Electronic spectrum (nm) [in acetonitrile]: 804 (5.35), 746 (4.92), 438 (3.88), 356 (4.22), 338 (3.98).

EXAMPLE 7

Synthesis of 2,6-di-tert-butyl-4-[3-chloro-5-(2,6-di-tert-butyl-4H-thiopyran-4-ylidene)penta-1,3-dienyl]thiopyrylium perchlorate [compound (6)] by process 1

64 mg of 2,6-di-tert-butyl-4-methylthiopyrylium perchlorate and 50 mg of 2-chloro-1-phenylimino-3-phenylimide-1-propene were heated in 1 ml of acetic anhydride over an oil bath at 110° C. for 5 minutes.

After the heating, 64 mg of 2,6-di-tert-butyl-4-methylthiopyrylium perchlorate and 100 mg of sodium acetate were added, and the mixture was heated over an oil bath at 110° C. for 10 minutes.

After the reaction mixture was allowed to cool, 50 ml of diethyl ether was added. The precipitated crystals were filtered, and recrystallized from ethanol to afford 68 mg (yield 55%) of crystals having a melting point of 224° to 226° C.

Elemental analysis for $C_{31}H_{44}S_2Cl_2O_4$:

|  | C | H | S |
|---|---|---|---|
| Calculated: | 60.47% | 7.20% | 10.41% |
| Found: | 60.49% | 7.31% | 10.27% |

Infrared absorption spectrum (wave number cm$^{-1}$): 1488, 1150, 743.

Electronic spectrum (nm) [in acetonitrile]: 806 (5.29), 746 (4.84), 438 (3.86), 360 (4.19), 310 (3.96).

EXAMPLE 8

Synthesis of 2,6-di-tert-butyl-4-[3-ethyl-5-(2,6-di-tert-butyl-4H-thiopyran-4-ylidene)penta-1,3-dienyl]thiopyrylium perchlorate [compound (3)]by process 1

61 mg of 2,6-di-tert-butyl-4-methylthiopyrylium perchlorate and 50 mg of 2-ethyl-1-phenylimine-3-phenylimide-1-propene were heated in 1 ml of acetic anhydride over an oil bath at 115° C. for 5 minutes.

After the heating, 60 mg of 2,6-di-tert-butyl-4-methylthiopyrylium perchlorate and 100 mg of sodium acetate were added, and the mixture was heated over an oil bath at 115° C. for 10 minutes.

After the reaction mixture was allowed to cool, 50 ml of diethyl ether was added. The precipitated crystals were filtered, and recrystallized from ethanol to afford 40 mg (yield 35%) of crystals having a melting point of 239° to 240° C.

Elemental analysis for $C_{33}H_{49}S_2ClO_4$:

|  | C | H | S |
|---|---|---|---|
| Calculated: | 65.05% | 8.11% | 10.53% |
| Found: | 65.33% | 8.08% | 10.65% |

Infrared absorption spectrum (wave number $cm^{-1}$): 1488, 1170, 1060, 740.

Electronic spectrum (nm) [in acetonitrile]: 807 (5.30), 748 (4.87), 446 (3.78), 360 (4.28), 309 (3.99).

EXAMPLE 9

One gram of poly-N-vinylcarbozale and 1.5 mg of each of the compounds (1) to (7) shown in the following table were dissolved in 10 g of 1,2-dichloroethane. The solution was coated by a rod bar on a film of polyethylene terephthalate having a vacuum-deposited layer of aluminum.

The coating was dried at 55° C. for 1 day to make a photosensitive material having a photoconductive layer.

The thickness of the photoconductive layer was about 2 μm. Since this photoconductive layer was transparent to visible light, the resulting photosensitive material exhibited the appearance of the polyethylene terephthalate film having the vacuum-deposited layer of aluminum in spite of the fact that the photoconductive layer was formed on it.

The resulting photosensitive material was charged to +400 V by applying a corona discharge of +6 KV using a commercially available corona discharge device. The charged surface was illuminated by a tungsten-filament lamp so that the intensity of light on the charged surface was 5 lux. The time (seconds) which elapsed until the surface potential of the surface of the photosensitive material reached 200 V was measured, and the amount of exposure was obtained. The thus obtained results are shown in the following table.

| Compounds | X | Half decay exposure E 178 (lux sec.) |
|---|---|---|
| 1 | H | 25 |
| 2 | —CH$_3$ | 31 |
| 3 | —CH$_2$CH$_3$ | 28 |
| 4 | phenyl | 18 |
| 5 | benzyl | 20 |
| 6 | Cl | 22 |
| 7 | Br | 26 |

EXAMPLE 10

A 5% aqueous solution of polyvinyl alcohol and polyvinylbenzyl-trimethyl ammonium chloride (weight ratio of polymers were 1:1) was coated on each side of a high quality paper in a dry amount of 3 g/m$^2$ to obtain an electroconductive high quality paper. A dispersion of the photoconductive composition shown below was coated on one surface of the thus coated paper in such an amount that the dry thickness became about 8 μm to obtain an electrophotographic paper.

| Coating Composition | |
|---|---|
| Zinc Oxide (Sazex 2000 : Tradename of zinc oxide produced by Sakai Kagaku Co., Ltd.) | 100 g |
| Styrene-Butadiene Copolymer (Pliolite S-5D : a copolymer produced by Goodyear Tire and Rubber Co.) | 16 g |
| Toluene (as a solvent) | 64 g |
| 2,6-Di-tert-butyl-4-[5-(2,6-di-tert-butyl-4H-thiopyran-4-ylidene)penta-1,3-dienyl]thiopyrylium perchlorate, [compound (1)] | 10 mg |
| Dichloromethane (as a solvent) | 10 g |

The resulting electrophotographic paper was charged to −400 V by applying a corona discharge in a dark place. The charged surface was exposed using a spectrograph and developed using a magnetic brush. A peak of spectral sensitivity was observed at a wave length of 830 μm in the near infrared region.

While the invention has been described in detail and with reference to specific embodiments thereof, it will be apparent to one skilled in the art that various changes and modifications can be made therein without departing from the spirit and scope thereof.

What is claimed is:

1. A photoconductive composition comprising a photoconductive material and a 2,6-di-tert-butyl-4-[5-(2,6-di-tert-butyl-4H-thiopyran-4-ylidene)penta-1,3-dienyl]-thiopyrylium salt of chemical structural formula (I)

$$(CH_3)_3C \quad \quad X \quad \quad C(CH_3)_3 \quad (I)$$
$$S^{\oplus} \quad \quad \quad \quad S$$
$$(CH_3)_3C \quad Z^{\ominus} \quad C(CH_3)_3$$

wherein $Z^{\ominus}$ represents an anion, and X represents a hydrogen atom, a halogen atom, an alkyl group or an aryl group.

2. The composition of claim 1 wherein X is a hydrogen atom.

3. The composition of claim 1 wherein X represents a substituted or unsubstituted straight or branched chain alkyl group having 1 to 15 carbon atoms, wherein the substituent is selected from the group consisting of an alkoxy group having 1 to 5 carbon atoms, a halogen atom and an aryl group having 6 to 15 carbon atoms.

4. The composition of claim 1 wherein X represents a substituted or unsubstituted aryl group having 6 to 11 carbon atoms and the substituent is selected from the group consisting of an alkoxy group having 1 to 5 carbon atoms, a halogen atom and an alkyl group having 1 to 5 carbon atoms.

5. The composition of claim 1 wherein X represents a hydrogen atom, a methyl group, an ethyl group, a phenyl group, a benzyl group, a chlorine atom or a bromine atom.

6. The composition of claim 1 wherein said photoconductive substance is at least one member selected from the group consisting of poly-N-vinylcarbazole, triarylamines polyarylmethanes and pyrazoline derivatives.

7. A 2,6-di-tert-butyl-4-[5-(2,6-di-tert-butyl-4H-thiopyran-4-ylidene)penta-1,3-dienyl]thiopyrylium salt of the following formula wherein $Z^\ominus$ represents an anion, and X represents a hydrogen atom, a halogen atom, an alkyl group or an aryl group.

8. The thiopyrylium salt of claim 7 wherein $Z^\ominus$ represents an anion of a strong acid having a pKa of not more than 5.

9. The thiopyrylium salt of claim 7 wherein said anion is a chloride ion, bromide ion, perchlorate ion, tetrafluoroborate ion, p-toluenesulfonate ion or trifluoroacetate ion.

10. The thiopyrylium salt of claim 7 wherein X represents a hydrogen atom, a linear or branched alkyl group having 1 to 15 carbon atoms, or a linear or branched alkyl group having 1 to 15 carbon atoms and a substituent selected from the group consisting of alkoxy groups having 1 to 5 carbon atoms, halogen atoms and aryl groups having 6 to 15 carbon atoms.

11. The thiopyrylium salt of claim 7 wherein X is a substituted or unsubstituted aryl group having 6 to 11 carbon atoms, said substituent being selected from the group consisting of an alkoxy group having 1 to 5 carbon atoms, a halogen atom and an alkyl group having 1 to 5 carbon atoms.

12. The thiopyrylium salt of claim 7 wherein X represents a hydrogen atom, a methyl group, an ethyl group, a phenyl group, a benzyl group, a chlorine atom or a bromine atom.

13. The thiopyrylium salt of claim 1 wherein said halogen atom is a fluorine, chlorine, bromine or iodine atom.

14. A process for preparing a 2,6-di-tert-butyl-4-[5-(2,6-di-tert-butyl-4H-thiopyran-4-ylidene)penta-1,3-dienyl]thiopyrylium salt of the formula (I)

wherein $Z^\ominus$ represents an anion, and X represents a hydrogen atom, a halogen atom, an alkyl group, or an aryl group, which comprises reacting a 2,6-di-tert-butyl-4-methylthiopyrylium salt of chemical structural formula (II)

wherein $Z^\ominus$ is as defined above, with a 1-phenylamino-3-phenylimino-1-propene of the formula (III)

wherein X is as defined above, or with a salt derived from said compound of formula (III) and an acid.

15. The process of claim 14 wherein said acid forming said salt with the 1-phenylamino-3-phenylimino-1-propene is an acid having a pKa of not more than 4.

16. The process of claim 14 wherein said acid forming said salt with the 1-phenylamino-3-phenylimino-1-propene is hydrochloric acid, hydrobromic acid or sulfuric acid.

17. The process of claim 14 wherein the reaction is carried out in a carboxylic acid anhydride in the presence of a base.

18. The process of claim 17 wherein said base is an amine.

19. The process of claim 17 wherein said carboxylic acid anhydride is acetic anhydride.

20. The process of claim 14 wherein the reaction is carried out in an amine.

21. A process for preparing a 2,6-di-tert-butyl-4-[5-(2,6-di-tert-butyl-4H-thiopyran-4-ylidene)penta-1,3-dienyl]thiopyrylium salt of the formula (I)

wherein $Z^\ominus$ represents an anion, and X represents a hydrogen atom, a halogen atom, an alkyl group or an aryl group, which comprises reacting a 2,6-di-tert-butyl-4-methylthiopyrylium salt of the formula (II)

wherein $Z^\ominus$ is as defined above, with a 1,1,3,3-tetraalkoxypropane of the formula (IV)

$$(RO)_2CHCHXCH(OR)_2 \quad (IV)$$

wherein X is as defined above, and R represents an alkyl group having 1 to 4 carbon atoms.

22. The process of claim 21 wherein the reaction is carried out in a carboxylic acid or a carboxylic acid anhydride in the presence of an amine.

23. The process of claim 22 wherein said carboxylic acid is acetic acid.

24. The process of claim 22 wherein said carboxylic acid anhydride is acetic acid anhydride.

25. The process of claims 14 or 21 wherein $Z^\ominus$ represents an anion of a strong acid having a pKa of not more than 5.

26. The process of claims 14 or 21 wherein said anion is a chloride ion, bromide ion, perchlorate ion tetrafluoroborate ion, p-toluenesulfonate ion, or trifluoroacetate ion.

27. The process of claims 14 or 21 wherein X represents a hydrogen atom, a substituted or unsubstituted straight chain or branched chain alkyl group having 1 to 15 carbon atoms, and the substituent is selected from the group consisting of an alkoxy group having 1 to 5 carbon atoms, a halogen atom and an aryl group having 6 to 15 carbon atoms.

28. The process of claims 14 or 21 wherein X represents a substituted or unsubstituted aryl group having 6 to 11 carbon atoms, and said substituent is selected from the group consisting of an alkoxy group having 1 to 5 carbon atoms, a halogen atom and an alkyl group having 1 to 5 carbon atoms.

29. The process of claims 14 or 21 wherein X represents a hydrogen atom, a methyl group, an ethyl group, a phenyl group, a benzyl group, a chlorine atom or a bromine atom.

* * * * *